United States Patent [19]

Saitoh et al.

[11] Patent Number: 4,690,926

[45] Date of Patent: Sep. 1, 1987

[54] BOXAZOMYCIN A AND B, NEW ANTIBIOTICS CONTAINING BENZOXAZOLE NUCLEUS

[75] Inventors: Kyoichiro Saitoh, Zushi; Masataka Konishi, Kawasaki; Koji Tomita, Tokyo, all of Japan

[73] Assignee: Bristol-Myers Company, New York, N.Y.

[21] Appl. No.: 825,498

[22] Filed: Feb. 3, 1986

[51] Int. Cl.$^4$ .................... A61K 31/42; C07D 263/58
[52] U.S. Cl. .................... 514/269; 435/119; 435/826; 544/298
[58] Field of Search .................... 544/298; 514/269

[56] References Cited

U.S. PATENT DOCUMENTS 3,927,023 12/1975 Brown et al. .................... 544/298 X Primary Examiner—Joseph P. Brust Attorney, Agent, or Firm—David M. Morse

[57] ABSTRACT

The novel antibiotics boxazomycin A and B, which have the formula:

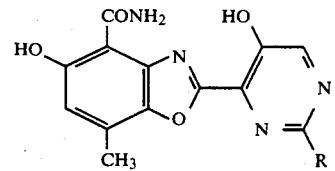

wherein R is —$CH_2OH$ for boxazomycin A; and R is —$CH_3$ for boxazomycin B. These new antibiotics, which are produced by cultivating a novel strain of Pseudonocardia (ATCC 53205), inhibit growth of aerobic Gram-positive bacteria and anaerobes with enhanced activity observed in acidic medium.

12 Claims, 4 Drawing Figures

13C-NMR SPECTRUM OF BOXAZOMYCIN A (Na SALT, 20 MHz IN $D_2O$)

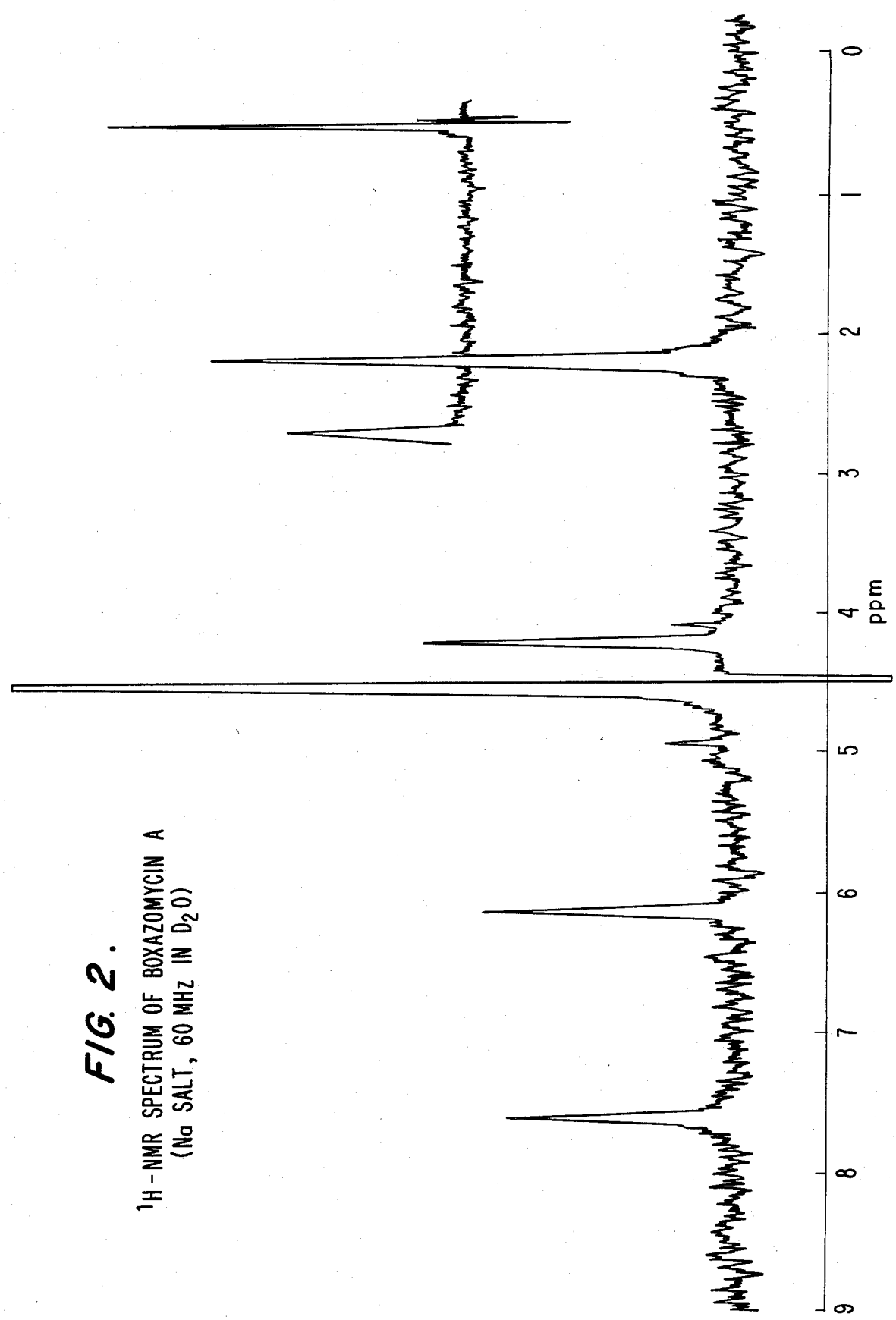

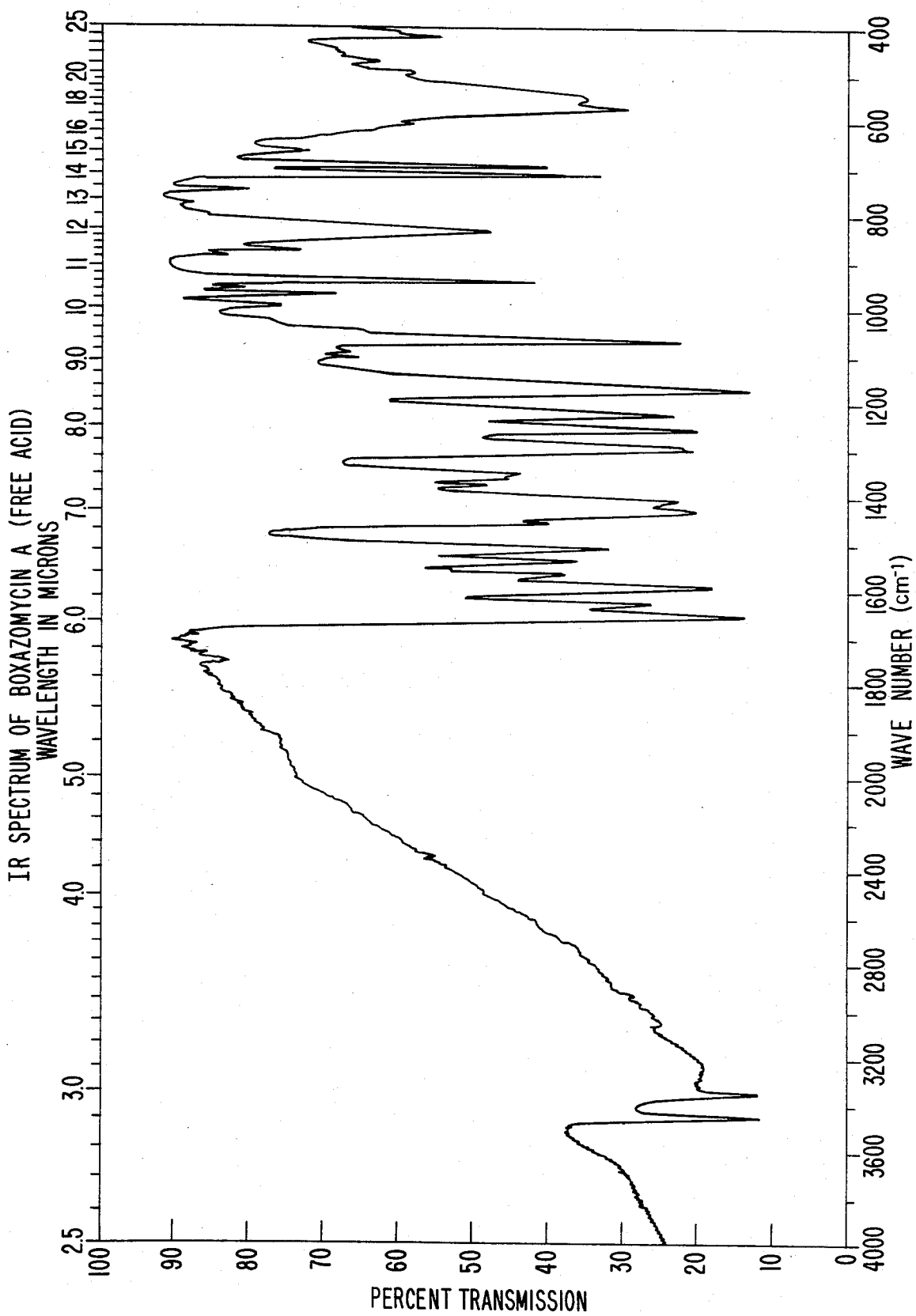

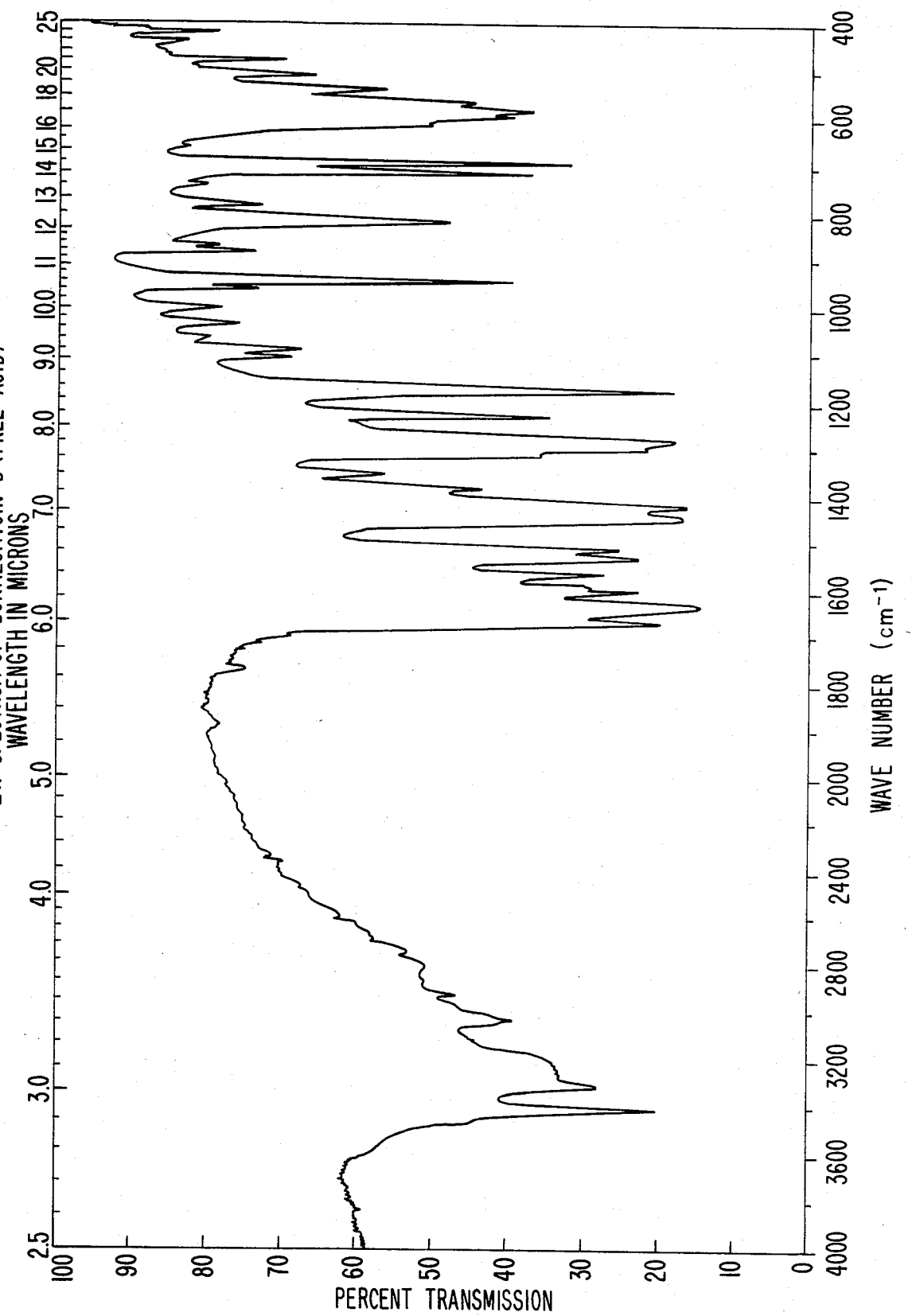

BOXAZOMYCIN A AND B, NEW ANTIBIOTICS CONTAINING BENZOXAZOLE NUCLEUS

FIELD OF THE INVENTION

This invention relates to novel antibiotic compounds, their production and recovery, their use in pharmaceutical compositions, and their use in treating microbial infections. This invention also relates to a novel microorganism that produces said novel antibiotic compounds when cultivated.

BACKGROUND OF THE INVENTION

The present invention relates to novel antibiotic compounds designated as boxazomycin A and B, to pharmaceutically acceptable derivatives thereof, to pharmaceutical compositions containing said compounds, to a process for the production of said compounds, and to a method for the treatment of infectious diseases caused by Gram-positive bacteria.

More particularly, the process for producing boxazomycin A and B relates to an aerobic fermentation process using a novel actinomycete strain No. G495-11 isolated from a soil sample collected in Taiwan. The morphological, cultural and physiological characteristics and the cellular chemical compositions described hereinafter indicate that strain No. G495-11 is classified as a species of the genus Pseudonocardia.

SUMMARY OF THE INVENTION

The new antibiotic compounds of this invention, boxazomycin A and B, have the following structures:

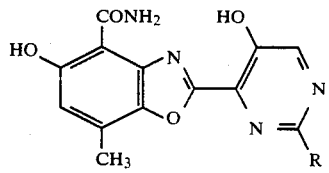

wherein R is —$CH_2OH$ for boxazomycin A; and R is —$CH_3$ for boxazomycin B.

Boxazomycin A and B, which are produced by cultivating actinomycete strain No. G495-11 (ATCC 53205), inhibit growth of aerobic Gram-positive bacteria and anaerobes with enhanced activity observed in acidic medium.

BRIEF DESCRIPTION OF THE DRAWINGS

FIG. 2 shows the proton magnetic resonance spectrum of the sodium salt of boxazomycin A in deuterium oxide.

FIG. 3 shows the infrared spectrum of boxazomycin A in the free acid form.

FIG. 4 shows the infrared spectrum of boxazomycin B in the free acid form.

DETAILED DESCRIPTION OF THE INVENTION

Figure 1:
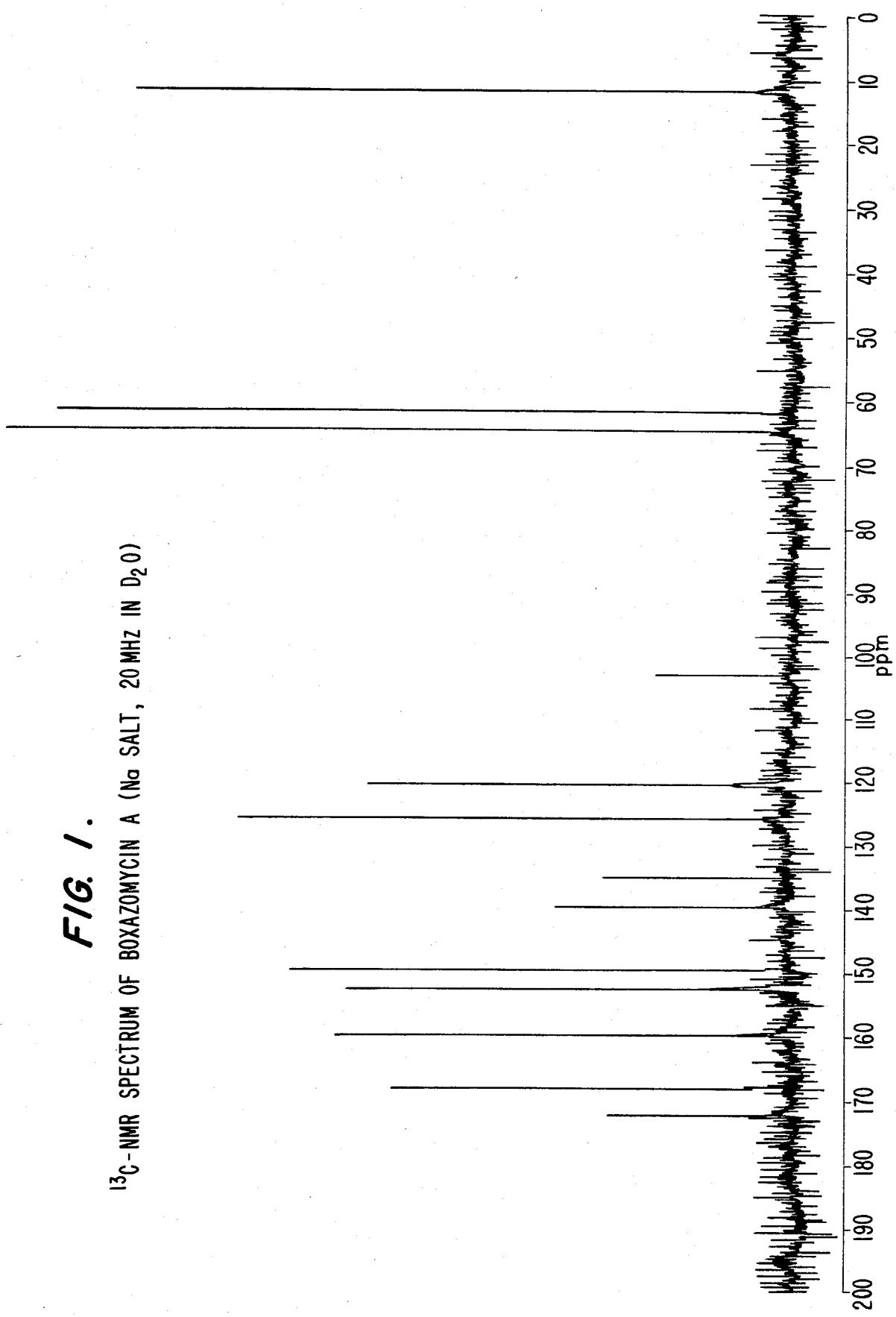
FIG. 1 shows the $^{13}C$ magnetic resonance spectrum of the sodium salt of boxazomycin A in deuterium oxide.

The novel antibiotic compounds boxazomycin A and B, named for their benzoxazole neclus, are fermentation products of actinomycete strain No. G495-11, which is classified as a species of the genus Pseudonocardia. A biologically pure culture of the organism has been deposited with the American Type Culture Collection, 12301 Parklawn Drive, Rockville, Md. 20852, and added to its permanent collection of microorganisms as ATCC 53205. The morphological, cultural and physiological characteristics and the cellular chemical compositions of strain No. G495-11 (ATCC 53205) indicate that the strain is classified as a species of the genus Pseudonocardia as described below:

Morphology

Strain No. G495-11 develops an abundance of long branched aerial mycelium (0.5 to 0.7 μm in width). The fragmentation of branched substrate mycelium occurs after one to three days, and the resulting elements are in the form of rods of various lengths and short branching filaments. The following characteristics are noted: (1) the segmentation of straight hyphae, bearing long chains of cylindrical spores (0.5 × 1.0–3.0 μm in size) with smooth surface, (2) constriction of hyphae to zig-zag form, (3) acropetal and basipetal buddings of blastospores on repeatedly branched aerial hyphae, occasionally with single swellings terminally or laterally. These structures are formed both on the aerial and substrate mycelia. The Gram-stain is positive, and acid-fast stain is negative.

Cultural and Physiological Characteristics

The cultural and physiological characteristics and the carbohydrate utilization profile are shown in TABLES 1, 2 and 3, respectively. Strain No. G495-11 grows well and forms thick white aerial mycelium on many agar media. A yellowish, non-carotinoid, lipophilic pigment is produced in various media. Strain No. G495-11 is resistant to lysozyme, ad sensitive to NaCl at 10%.

TABLE 1

| Cultural Characteristics* of Strain No. G495-11 | |
|---|---|
| Tryptone-yeast extract broth (ISP No. 1) | G**: No turbidity; whitish pellicle and colorless sediment<br>D: None |
| Sucrose-nitrate agar (Czapek's agar) | G: Poor<br>R: Yellowish white (92)<br>A: No or scant<br>D: None |
| Glucose-asparagine agar | G: Moderate<br>R: Yellowish white (92) to brilliant orange yellow (67)<br>A: Moderate; white (263)<br>D: Pale yellow (89) |
| Glycerol-asparagine agar (ISP No. 5) | G: Abundant<br>R: Deep yellow (85) to light brown (57)<br>A: Abundant; white (263) to light yellow (86). Formation of blastospores<br>D: Vivid greenish yellow (97) |
| Inorganic salts-starch agar (ISP No. 4) | G: Poor<br>R: Yellowish white (92)<br>A: No or scant<br>D: None |
| Tyrosine agar (ISP No. 7) | G: Abundant<br>R: Strong yellow (84) or dark olive brown (96)<br>A: Abundant; white (263) to light greenish yellow (101)<br>D: Moderate yellow (87) |
| Nutrient agar | G: Moderate<br>R: Yellowish white (92)<br>A: Scant; white (263)<br>D: Pale yellow (89) |
| Yeast extract-malt extract agar (ISP No. 2) | G: Abundant<br>R: Brilliant yellow (83) to brownish orange (54)<br>A: Moderate; white (263)<br>D: Dark orange yellow (72) |
| Oatmeal agar (ISP No. 3) | G: Poor<br>R: Pale orange yellow (73) |

TABLE 1-continued

Cultural Characteristics* of Strain No. G495-11

| | | |
|---|---|---|
| Bennett's agar | A: | No or scant |
| | D: | None |
| | G: | Abundant |
| | R: | Light yellow (86) to deep orange (51) |
| | A: | Abundant; white (263) |
| | D: | Dark yellow (88) |
| Peptone-yeast extract-iron agar (ISP No. 6) | G: | Moderate |
| | R: | Strong yellow (84) |
| | A: | None |
| | D: | None |

*observed during incubation at 28° C. for 2 weeks.
**abbreviation: G - Growth; R - Reverse color; A - Aerial mycelium; D - Diffusible pigment
***Color and number in parentheses follow the color standard in "Kelly, K. L. & D. B. Judd: ISCC-NBS color-name charts illustrated with Centroid Colors. US Dept. of Comm. Cir. 553, Washington, D.C., Nov., 1975".

TABLE 2

Physiological Characteristics of Strain No. G495-11

| Test | Response | Method or medium used |
|---|---|---|
| Temperature for growth | Range: 12° C.-40° C. Optimum: 25° C.-32° C. No growth: 10° C., 42° C. | Bennett's agar |
| Gelatin liquefaction | Positive (slow) | 1% malt extract, 0.4% yeast extract, 0.4% glucose, 20% gelatin |
| Starch hydrolysis | Negative | Starch agar plate |
| Reactions in skimmed milk | Peptonized and not coagulated | Difco skimmed milk |
| Formation of melanoid pigment | Negative | Tyrosine agar, peptone-yeast extract-iron agar, and tryptone-yeast extract broth |
| Tyrosinase reaction | Negative | Arai's method* |
| Nitrate reduction | Negative | 0.5% yeast extract, 1% glucose, 0.5% KNO$_3$, 0.1% CaCO$_3$. |
| pH tolerance | Growth in pH 4.5-11.0 | Yeast extract-malt extract agar |
| NaCl tolerance | Growth at 7% or less | Basal medium: 1% yeast extract, 2% soluble starch, 1.5% agar |
| Lysozyme tolerance | Resistant to 0.01% | Trypticase soy broth plus 1.5% agar |
| Yellow lipophilic pigment | Non-carotinoid | Pridham-Gottlieb's basal medium supplemented with xylose or galactose at 5 g/L. |

*Arai, T. and Y. Mikami: Chromogenicity of *Streptomyces*, Appl. Microbiol. 23:402-406, 1972.

TABLE 3

Carbohydrate Utilization of Strain No. G495-11

| | |
|---|---|
| Glycerol | + |
| D(−)-Arabinose | + |
| L(+)-Arabinose | + |
| D-Xylose | + |
| D-Ribose | + |
| L-Rhamnose | − |
| D-Glucose | + |
| D-Galactose | + |
| D-Fructose | + |
| D-Mannose | + |
| L(−)-Sorbose | − |
| Sucrose | − |
| Lactose | + |
| Cellobiose | + |
| Melibiose | − |
| Trehalose | + |
| Raffinose | − |
| D(+)-Melezitose | − |
| Soluble starch | − |
| Cellulose | − |
| Dulcitol | − |
| Inositol | + |
| D-Mannitol | + |
| D-Sorbitol | − |

TABLE 3-continued

Carbohydrate Utilization of Strain No. G495-11

| | |
|---|---|
| Salicin | − |

These results were observed after incubation at 28° C. for 2 weeks.
Basal medium: Pridham-Gottlieb's inorganic medium, supplemented with yeast extract at 0.2 g/L
Abbreviation: +: positive utilization, −: negative utilization.

Cellular Chemical Analyses

The following cellular components were analyzed: amino acid in purified cell wall; sugars in whole cell hydrolyzate; N-acyl type of peptidoglycan; phospholipid; and nocardomycolic acid (LCN-A). The results are shown in TABLE 4. Strain No. G495-11 has the composition of cell wall Type IV-A and phospholipid Type IV. The N-acyl type of peptidoglycan is acetyl. Nocardo-mycolic acid is not contained.

TABLE 4

Cell Chemistry of Strain No. G495-11

| | Diagnostic Component |
|---|---|
| Purified cell wall | Meso-diaminopimelic acid |
| Whole cell hydrolyzate | Arabinose and galactose |
| N—Acyl type of peptidoglycan (glycolate test) | Acetyl |
| Phospholipid | Phosphatidylethanolamine (PE), phosphatidylglucosamine (Glu NU), and phosphatidylcholine (PC)-trace |
| Nocardo-mycolic acid | Absent |

Occurrence of Variants

The orignial culture of strain No. G495-11, which was maintained at −20° C. for 8 years, occurred in the following three tentative morphotypes:

Type 1*: Formation of long and well-branched stable aerial mycelium

Type 2*: Formation of short rudimentary aerial mycelium

Type 3*: Lacking the ability to form aerial mycelium
* Type 1 includes a purified culture, strain No. G495-11.

A variant No. 028 of Type 3 develops true vegetative mycelium which fragments into short filaments and rods. The surface of growth is wrinkled, granular or butyrous on the descriptive agar media. The physiological characteristics, such as formation of yellow pigment, profile of carbohydrate utilization and productivity of antibiotic boxazomycin are well consistent with the aerial mycelium-forming strain No. G495-11. A difference from strain No. G495-11 is observed in positive nitrate reduction of variant No. 028.

Toxonomic Position

Based on the major characteristics mentioned above, strain No. G495-11 was compared with genera Pseudonocardia, Micropolyspora, Saccharomonospora, Actinopolyspora, Saccharopolyspora and two atypical species of genus Nocardia, *N. autotrophica* and *N. orientalis*. Morphologically, strain No. G495-11 forms segmented straight long hyphae with total sporulation, blastospore-like segmented short hyphae with apical swelling, and zigzag constricting hyphae. Although the two know species of genus Pseudonocardia are reported to have Type P-III phospholipid including phosphatidylcholine, the other major characteristics indicated that strain No. G495-11 is a species of the genus Pseudonocardia.

The following example illustrates the best mode contemplated for carrying out the invention.

EXAMPLE

Antibiotic Production

The stock culture of strain No. G495-11 was maintained on an agar slant having a medium composition of 1% malt extract, 0.4% glucose, 0.4% yeast extract, 0.05% $CaCO_3$ and 1.6% agar (pH 7.0). The culture was incubated at 28° C. for two weeks. A well grown agar slant was used to inoculate a vegetative medium consisting of 3% glucose, 3% soybean meal, 0.5% NaCl and 0.1% $CaCO_3$. The pH of the medium was adjusted to 7.0 before sterilization. After incubation at 28° C. for 2 days on a rotary shaker (250 rpm), 5 mL of the growth was transferred into a 500 mL Erlenmeyer flask containing 100 mL of a production medium having the same composition as the vegetative medium. The antibiotic activity in the fermentation broth was monitored by the paper disc-agar diffusion method using *Bacillus subtilis* PCI 219 as the test organism. The fermentation was continued for 4 to 5 days at 28° C. on a rotary shaker and the production of boxazomycin reached a maximum of 50 mcg/mL.

Isolation and Purification

The harvested broth (128 L, pH 7.8) was separated to mycelial cake and supernatant in a Sharpless centrifuge. The mycelial cake was stirred for 30 minutes with methanol (30 L) and the methanolic extract evaporated in vacuo to yield an aqueous concentrate. This was combined with the supernatant obtained above, adjusted to pH 2.0 and extracted twice with ethyl acetate (75 L each). After washing with water (50 L), the ethyl acetate extract was shaken with dilute NaOH (35 L, pH 8.6) to transfer the activity into the aqueous solution. Upon acidification to pH 2.0 with 6N hydrochloric acid, a crude yellow solid of boxazomycin complex precipitated from the aqueous solution (24.1 g). Part of this solid (22 g) was dissolved in alkaline water (350 mL, pH 10.0) and the insoluble material was removed by filtration. Acidification of the filtrate to pH 5.0 deposited a partially purified solid complex (12.2 g) which consisted of boxazomycin A (the major component) and B (the minor component), as revealed by thin layer chromatography (TLC) (system BT-103: $CHCl_3$—MeOH—AcOH=80:20:4 in volume). The complex solid (12.2 g) was dissolved in a small volume of $CHCl_3$—MeOH—AcOH (80:20:4) mixture and applied on a silica gel column (6.7×50 cm) which had been equilibrated with the same solvent. The column was eluted with the above-mentioned solvent mixture, and the eluate was collected in fractions (20 mL) and monitored by bioassay against *B. subtilis* PCI-219 and TLC (BT-103). Fractions containing boxazomycin B (Fr. Nos. 23–27) were combined, concentrated in vacuo and lyophilized to give a pale yellow, homogeneous solid (0.19 g). Fraction Nos. 29–60 were similarly worked up to afford pure boxazomycin A solid (2.37 g). For crystallization, boxazomycin A (160 mg) was dissolved in 250 mL of hot methanol, filtered, and the filtrate was allowed to stand at room temperature to deposit pale yellow, fine needles of boxazomycin A free acid (85 mg). One gram of the above solid sample was dissolved in methanolic 0.2N NaOH (40 mL) at 70° C. and the insolubles were removed by filtration. Upon standing at room temperature, di-sodium salt of boxazomycin A crystallized as orange columns (500 mg) which were recrystallized from aqueous methanol (MeOH—$H_2O$=10:3). The yield was 305 mg.

Physico-chemical properties

Boxazomycin A and B are yellow, weakly acidic substances showing similar physico-chemical properties. The two components are differentiated by two TLC systems (TABLES 5 and 6). Boxazomycin A was isolated as crystals both in free acid and di-sodium salt forms, while boxazomycin B has been obtained as an amorphous powder. Boxazomycin A and B free acids are readily soluble in alkaline water and dimethylformamide, slightly soluble in water, methanol, ethanol and acetone, but practically insoluble in ethyl acetate, chloroform, benzene and n-hexane. Boxazomycin A di-sodium salt is soluble in water. They gave a positive response to ferric chloride, concentrated $H_2SO_4$ and iodine reagents but were negative in ninhydrin and anthrone tests. Molecular formulae of $C_{14}H_{12}N_4O_5$ and $C_{14}H_{12}N_4O_4$ were assigned to boxazomycin A and B, respectively, from their mass spectral and microanalytical data. Both components exhibited a similar UV spectrum in neutral and alkaline solutions. The physico-chemical data of boxazomycin A and B are summarized in TABLES 5 and 6, respectively. Their IR spectra (FIGS. 3 and 4) exhibited primary amide bands at 1650 and 1630 $cm^{-1}$, and OH and/or NH absorptions at 3350 and 3450 $cm^{-1}$. The $^1H$-NMR spectrum of boxazomycin A (FIG. 2) showed the presence of one methyl ($\delta 2.25$ ppm, s), one methylene ($\delta 4.40$ ppm, s) and two aromatic protons ($\delta 6.35$ ppm, s and 7.85 ppm, s). The $^1H$-NMR spectrum of boxazomycin B differed from that of boxazomycin A only in the presence of an additional methyl group ($\delta 2.20$ ppm, s) instead of the methylene group of the latter. The $^{13}C$-NMR spectrum of boxazomycin A (FIG. 1) displayed 12 carbon signals, with two of them showing double intensity. Upon acetylation in pyridine, boxazomycin A afforded crystalline tetra-N-acetate (MS: molecular ion at m/z 484).

TABLE 5

Physico-Chemical Properties of Boxazomycin A

| | Boxazomycin A | |
|---|---|---|
| | Free acid | Di—Na salt |
| Nature | Pale yellow needles | Orange columns |
| M.P. | >275° C. (dec.) | >270° C. (dec.) |
| Microanalysis Calcd for | $C_{14}H_{12}N_4O_5 \cdot \frac{1}{2}CH_3OH$ | $C_{14}H_{10}N_4O_5 Na_2—2H_2O$ |
| | C 52.41; H 4.22; N 16.87 | C 42.43; H 3.56; N 14.41; Na 11.60 |
| Found | C 52.80; H 4.21; N 16.59 | C 41.99; H 3.24; N 14.42; Na 12.21 |
| EI-MS | 316 (M), 299, 215 | |
| UV $\lambda_{max}$ nm($\epsilon$) in EtOH—DMF (95:5) | 364 (13,500) $379^{sh}$(12,600) $420^{sh}$(6,100) | |
| in 0.1N NaOH | 219 (28,700) $230^{sh}$(24,800) $259^{sh}$(13,100) 403 (20,200) | |
| TLC ($SiO_2$): RF n BuOH—AcOH—$H_2O$ (3:1:1) | 0.14 | |
| $CHCl_3$—MeOH—AcOH (80:20:4) | 0.22 | |

TABLE 6

Physico-Chemical Properties of Boxazomycin B

| | Boxazomycin B Free acid |
|---|---|
| Nature | Pale yellow powder |
| M.P. | >270° C. (dec.) |
| Microanalysis | $C_{14}H_{12}N_4O_4$ |
| Calcd for | C 56.00; H 4.03; N 18.66 |
| Found | C 55.63; H 3.82; N 18.34 |
| EI-MS | 300 (M), 283, 215 |
| UV $\lambda_{max}$ nm($\epsilon$) in EtOH—DMF (95:5) | 364 (14,800) $379^{sh}$(12,800) $420^{sh}$(2,200) |
| in 0.1N NaOH | 219 (28,700) $230^{sh}$(24,100) $259^{sh}$(11,600) 403 (21,100) |
| TLC ($SiO_2$): RF n BuOH—AcOH—$H_2O$ (3:1:1) | 0.44 |
| $CHCl_3$—MeOH—AcOH (80:20:4) | 0.54 |

Antimicrobial Activity and Toxicity

The minimum inhibitory concentrations (MICs) of boxazomycin A and B were determined by the serial agar dilution method. Nutrient agar (Eiken) was used for aerobic bacteria, GC medium (Eiken) for fastidiuous organisms and GAM agar medium (Nissui) for anaerobic bacteria. TABLE 7 shows the in vitro antibacterial activity of boxazomycin A and B in comparison with kanamycin. The two components of boxazomycin showed similar antibacterial spectra, inhibiting Gram-positive aerobic and Gram-positive/Gram-negative anaerobic organisms, while kanamycin was inactive against anaerobes. The intrinsic activity of boxazomycin A was comparable to or slightly higher than that of boxazomycin B. As shown in TABLE 8, boxazomycin A and B showed enhanced activity in acidic media, especially against anaerobic bacteria.

The in vivo efficacy of boxazomycin A was assessed in an experimental model of mice infected by strains of *Staphylococcus aureus* and *Clostridium perfringens*. Mice were challenged with a $100 \times LD_{50}$ dose of the pathogens in a 5% suspension of hog gastric mucin (American Laboratory, Omaha, Nebr.). Boxazomycin A was dissolved in saline and administered to mice intramuscularly just before the bacterial challenge. As shown in TABLE 9, boxazomycin A showed protective effect in mice against both infections, but its in vivo efficacy was lower than that expected from its in vitro activity. Boxazomycin A did not show any toxic symptoms up to a dose of 400 mg/kg (i.m.).

TABLE 7

Antibacterial Activity of Boxazomycin A and B

| | | MIC (mcg/mL) | | |
|---|---|---|---|---|
| | | Boxazomycin | | |
| Test organisms | Test medium | A | B | Kanamycin |
| *Staphylococcus aureus* 209P | A | 0.4 | 0.4 | 0.4 |
| *S. aureus* Smith | A | 0.4 | 0.4 | 0.8 |
| *S. aureus* BX-1633[b] | A | 0.8 | 0.8 | 0.8 |
| *S. aureus* A20239[c] | A | 0.4 | 0.8 | >100 |
| *S. aureus* A22421[d] | A | 0.8 | 0.8 | 0.8 |
| *S. epidermidis* A22547[c] | A | 0.4 | 0.2 | 25 |
| *Streptococcus pyogenes* S-23 | B | 3.1 | 12.5 | 25 |
| *S. pneumoniae* IID | B | 3.1 | 25 | 25 |
| *S. faecalis* A9612 | A | 0.8 | 3.1 | 25 |
| *Micrococcus luteus* PCI1001 | A | 0.4 | 0.8 | 3.1 |
| *Bacillus subtilis* PCI 219 | A | 3.1 | 1.6 | 0.2 |
| *Mycobacterium smegmatis* 607 | A | 1.6 | 3.1 | 0.8 |
| *M. phlei* D88 | A | 0.8 | 1.6 | 1.6 |
| *M. smegmatis* 607 D46[c] | A | 1.6 | 3.1 | >100 |
| *Escherichia coli* NIHJ | A | >100 | >100 | 1.6 |
| *Klebsiella pneumoniae* D-11 | A | >100 | >100 | 0.4 |
| *Proteus mirabilis* A9554 | A | >100 | >100 | 3.1 |
| *Pseudomonas aeruginosa* D-113 | A | >100 | >100 | 25 |

TABLE 7-continued

Antibacterial Activity of Boxazomycin A and B

| | | MIC (mcg/mL) | | |
|---|---|---|---|---|
| | | Boxazomycin | | |
| Test organisms | Test medium | A | B | Kanamycin |
| Neisseria gonorrhoeae A15112 | B | >100 | >100 | 0.4 |
| Haemophilus influenzae A9729 | B | >100 | >100 | 0.4 |
| Clostridium difficile A21675[c] | C | 3.1 | 6.3 | >50 |
| C. perfringens A9635 | C | 3.1 | 12.5 | >50 |
| Propionibacterium acnes A21933 | C | 3.1 | 6.3 | >50 |
| Peptostreptococcus anaerobius A21905 | C | 3.1 | 6.3 | >50 |
| B. fragilis A22534[b] | C | 3.1 | 12.5 | 50 |
| Bacteroides fragilis A22693 | C | 6.3 | 12.5 | 50 |

[a]A: Nutrient agar (Eiken) B: GC medium (Eiken) C: GA agar (Nissui)
[b]β-Lactamase producer
[c]Kanamycin-resistant
[d]Methicillin-resistant
[e]Clindamycin-resistant

TABLE 8

Effect of pH on Antimicrobial Activity

| | MIC (mcg/mL) | | | |
|---|---|---|---|---|
| | Boxazomycin A | | Boxazomycin B | |
| | pH 6 | pH 7 | pH 6 | pH 7 |
| B. subtilis PCI 219 | 0.8 | 6.3 | 0.2 | 1.6 |
| M. luteus PCI 1001 | 0.1 | 0.4 | 0.2 | 0.8 |
| S. aureus 209P | 0.4 | 0.8 | 0.2 | 0.8 |
| E. coli NIHJ | >100 | >100 | >100 | >100 |
| K. pneumoniae D11 | >100 | >100 | >100 | >100 |
| C. perfringens A9635 | 0.2 | 3.1 | 0.4 | 6.3 |
| P. acnes A21933 | 0.4 | 6.3 | 0.2 | 6.3 |
| B. fragilis A20926 | 0.05 | 3.1 | 0.1 | 3.1 |
| S. necrophorus A15202 | 0.4 | 3.1 | 0.4 | 6.3 |

TABLE 9

In Vivo Activity of Boxazomycin A
PD$_{50}$ (mg/kg, i.m.)

| Test organisms | Boxazomycin A | Kanamycin |
|---|---|---|
| Staphylococcus aureus Smith | 400 | 1.4 |
| Clostridium perfringens A9635 | 220 | — |

As shown above, boxazomycin A and B possess antimicrobial activity and are thus useful in the therapeutic treatment of mammals and other animals for infectious diseases caused by such microorganisms. Additionally, the compounds may be utilized for other conventional applications of antimicrobial agents such as disinfecting medical and dental equipment.

The present invention, therefore, provides a method for therapeutically treating an animal host affected by a microbial infection, which method comprises administering to said host an effective antimicrobial dose of boxazomycin A or B, or a pharmaceutical composition thereof.

In another aspect, the present invention provides a pharmaceutical composition which comprises an effective antimicrobial amount of boxazomycin A or B in combination with an inert pharmaceutically acceptable carrier or diluent. These compositions may be made up in any pharmaceutical form appropriate for the desired use, e.g., oral or parenteral administration.

Preparations for parenteral administration include sterile aqueous or non-aqueous solutions, suspensions or emulsions. They may also be manufactured in the form of sterile solid compositions which can be dissolved in sterile water, physiological saline or some other sterile injectable medium immediately before use. Preparations for oral administration include tablets, capsules, pills, powders, granules and liquid forms such as solutions, emulsions, suspensions, syrups and elixirs. Some of the liquid forms may also be appropriate for topical application.

This invention also contemplates use of boxazomycin A and B in the form of nontoxic acid addition salts with a variety of organic and inorganic salt-forming reagents. Such nontoxic salts are well known to those skilled in the art, and include acid addition salts formed with such pharmaceutically acceptable organic or inorganic acids as sulfuric, phosphoric, hydrochloric, acetic, propionic, oleic, palmitic, citric, succinic, tartaric, glutamic, pantothenic, et. These salts are formed, isolated, purified and formulated by the methods generally employed in salt formation for antibiotics, and are employed in the same manner as the boxazomycin A and B compounds per se.

It will be appreciated that the actual preferred amounts of boxazomycin A and B antibiotics used will vary according to the particular component, the particular compositions formulated, the mode of application, and the particular situs, host and disease being treated. Many factors that modify the action of the drug will be taken into account by those skilled in the art, for example, age, body weight, sex, diet, time of administration, route of administration, rate of excretion, condition of the host, drug combinations, reaction sensitivities, and severity of the disease. Administrations can be carried out continuously or periodically within the maximum tolerated dose. Optimal application rates for a given set of conditions can be ascertained by those skilled in the art using conventional dosage determination tests in view of the above guidelines.

We claim:

1. The antibiotic compound boxazomycin A which has the structure:

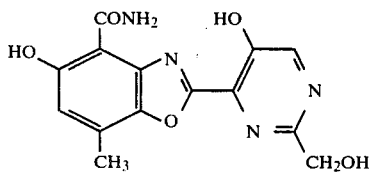

or a nontoxic salt thereof.

2. The compound of claim 1 in the form of a nontoxic acid addition salt.

3. The antibiotic compound boxazomycin B which has the structure:

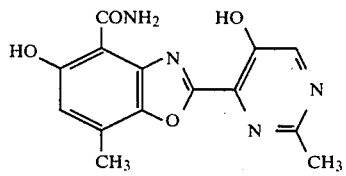

or a nontoxic acid addition salt thereof.

4. The compound of claim 3 in the form of a nontoxic acid addition salt.

5. A method for therapeutically treating a host animal affected by a microbial infection which comprises administering to said host animal an antimicrobially effective amount of boxazomycin A of the formula

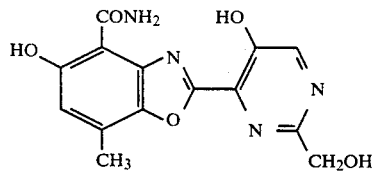

or a nontoxic salt thereof, or a pharmaceutical composition thereof.

6. The method of claim 5, wherein boxazomycin A is in the form of a nontoxic acid addition salt.

7. A method for therapeutically treating a host animal affected by a microbial infection which comprises administering to said host animal an antimicrobially effective amount of boxazomycin B of the formula

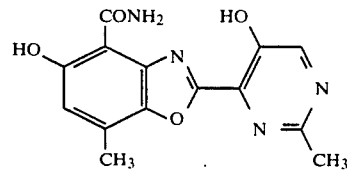

or a nontoxic acid addition salt thereof, or a pharmaceutical composition thereof.

8. The method of claim 7, wherein said boxazomycin B is in the form of a nontoxic acid addition salt.

9. A pharmaceutical composition comprising an antimicrobially effective amount of boxazomycin A of the formula

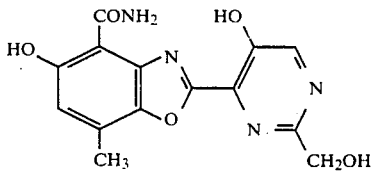

or a nontoxic salt thereof.

10. The pharmaceutical composition of claim 9 wherein said boxazomycin A is in the form a nontoxic acid addition salt.

11. A pharmaceutical composition comprising an antimicrobially effective amount of boxazomycin B of the formula

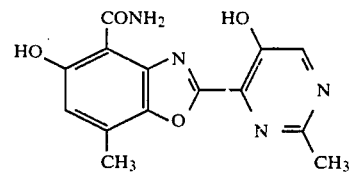

or a nontoxic acid addition salt thereof.

12. The pharmaceutical composition of claim 11, wherein boxazomycin B is in the form of a nontoxic acid addition salt.

* * * * *